United States Patent [19]

Fixel

[11] Patent Number: 5,112,333
[45] Date of Patent: May 12, 1992

[54] INTRAMEDULLARY NAIL

[76] Inventor: Irving E. Fixel, 111 N. 31st Ave., Hollywood, Fla. 33021

[21] Appl. No.: 476,977

[22] Filed: Feb. 7, 1990

[51] Int. Cl.⁵ ............................................. A61B 17/56
[52] U.S. Cl. ......................................... 606/62; 606/63
[58] Field of Search ................................. 606/60–71, 606/89, 91, 105

[56] References Cited

U.S. PATENT DOCUMENTS

| | | | |
|---|---|---|---|
| 3,024,785 | 3/1962 | Dobelle | 606/63 |
| 3,779,239 | 12/1973 | Fischer | 606/63 |
| 3,986,504 | 10/1976 | Avila | 606/63 |
| 4,091,806 | 5/1978 | Aginsky | 606/63 |
| 4,237,875 | 12/1980 | Termanini | 606/63 |
| 4,275,717 | 6/1981 | Bolesky | 606/63 |
| 4,530,355 | 7/1985 | Griggs | 606/105 |
| 4,574,795 | 3/1986 | Georges | 606/64 |
| 4,776,330 | 10/1988 | Chapman | 606/64 |
| 4,858,602 | 8/1989 | Seidel | 606/60 |
| 4,875,475 | 10/1989 | Comte | 606/64 |
| 4,946,459 | 8/1990 | Bradshaw | 606/63 |

FOREIGN PATENT DOCUMENTS

| | | | |
|---|---|---|---|
| 0321170 | 6/1989 | European Pat. Off. | 606/62 |
| 2342710 | 9/1977 | France | 606/67 |

Primary Examiner—Robert A. Hafer
Assistant Examiner—Michael Brown
Attorney, Agent, or Firm—Richard M. Saccocio

[57] ABSTRACT

A two-piece intramedullary nail is provided having a stem portion and a rod portion. The distal and proximal ends of a femur are compressingly secured by the intramedullary nail by lag screw threads at the stem portion and a stepped portion at the proximal end of the intramedullary nail. A groove and key fit up between the stem portion and the rod portion prevents rotation of the two parts of the intramedullary nail. Elongated slots within the rod member and the stem member provide for openings through which fastening devices may easily be located and passed therethrough in order to secure broken fragments of the femur to the femur. An opening in the proximal end of the intramedullary nail provides for fit up of a hip plate and screw prosthesis or a femoral head hip prosthesis while providing structural support to the cylinder to plate connection thereof.

15 Claims, 3 Drawing Sheets

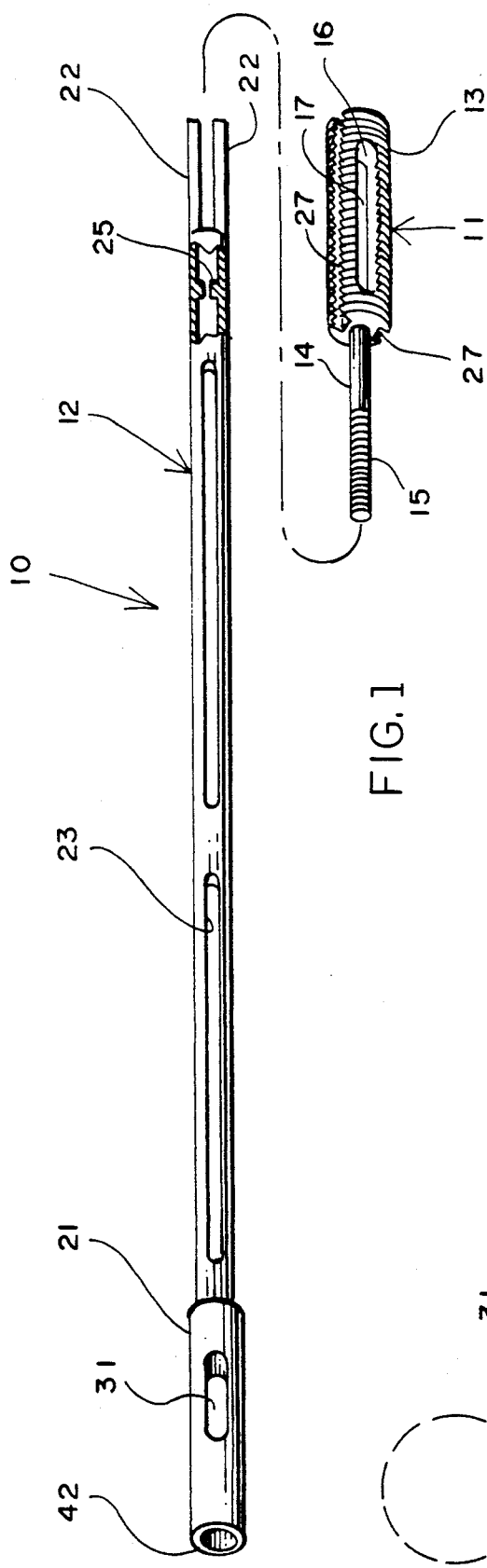
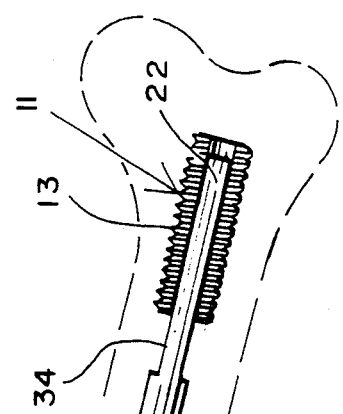
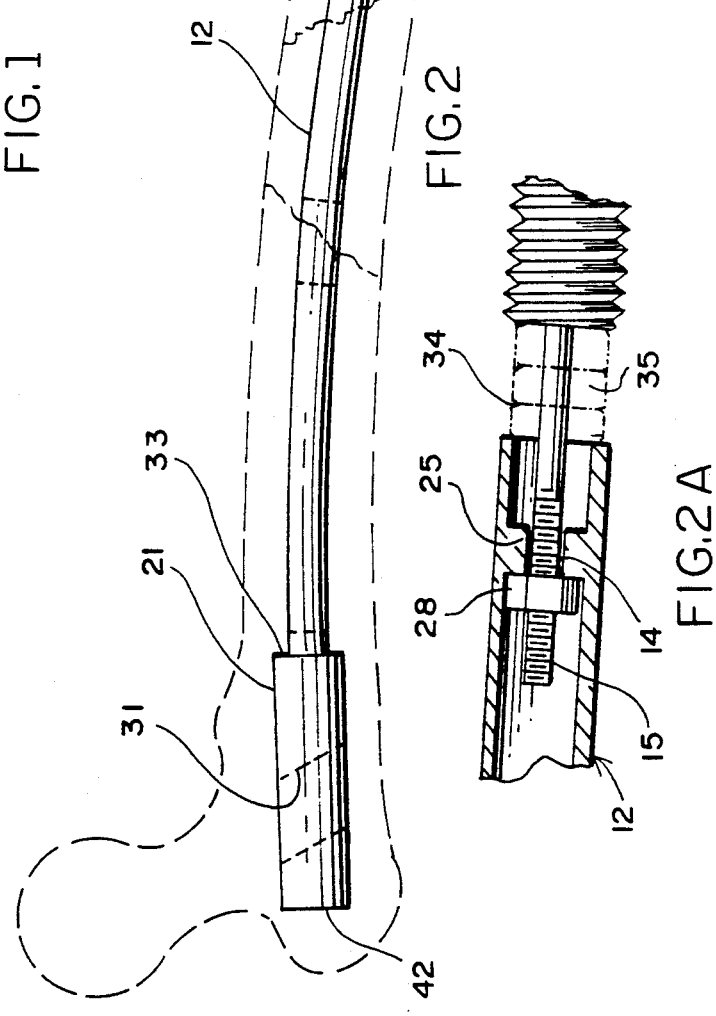
FIG.1
FIG.2
FIG.2A

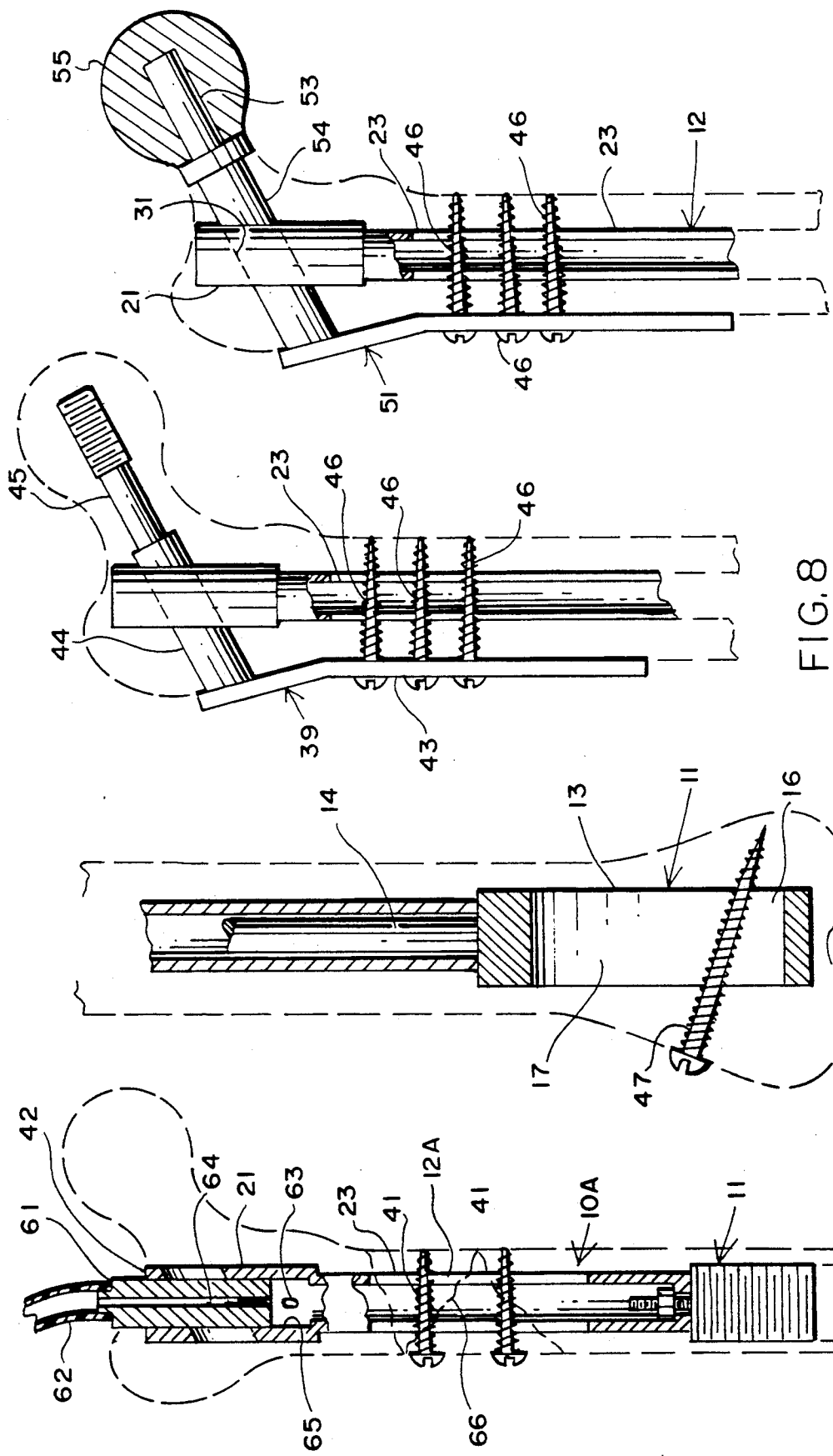

INTRAMEDULLARY NAIL

BACKGROUND OF THE INVENTION

1. Field of the Invention

This invention pertains in general to the field of bone fixation devices and in particular to an intramedullary nail which may be used for reconstruction of fractures of the femoral or the tibia bones.

2. Description of the Prior Art

Closed transverse fractures in the middle one third of the femur and/or the tibia have historically been reconstructed using an intramedullary nail. For these types of simple fractures, the prior art intramedullary nail comprising an elongated hollow rod either slotted or unslotted have successfully been used to reconstruct such broken bones. Usually, and more so in the present prior art, a locking nail has been utilized. A locking nail involves the use of transverse screws passing through the bone and the intramedullary nail at both of the proximal and distal locations of the tibia or the femur. Such locking provisions provide for proper alignment of the bones as well as provide for the proper length fixation of the bones after the break.

On the other hand, comminuted fractures, segmental fractures, fractures with bone loss, and rotationally unstable fractures of these bones are much more difficult to treat using the prior art intramedullary nails. With any of these types of fractures, there is the distinct possibility that non-union, rotation and displacement of bone fragments may result. Improper angularity may include transverse angularity where the broken portions of the bone are transversely offset relative to each other; axial angularity involves improper alignment of the axial centerline of the broken portions of the bone; and, rotational angularity involves improper rotational alignment of one broken portion of the bone relative to the other portion of the bone. All of these degrees of angularity must be properly aligned in order to properly reconstruct a broken femur or tibia.

In the prior art intramedullary nails, the locking provision of the same provides the only means to assure proper angularity and length fixation of reconstructed bones. In this regard, as previously stated, the prior art intramedullary nails are provided with one or more through transverse holes at each end of the nail for purposes of inserting a screw fastener therethrough after the intramedullary nail has been fitted within the broken portions of the bones. Once the intramedullary nail is fitted within the bone, the exact location of the through transverse holes at either end thereof is not observable to the operating physician. Therefore, means must be provided to enable the physician to locate these holes preciesly and insert threaded fastener through the bone and into and through the transverse holes. This is not an easy task. Location of the proximal transverse hole or holes is relative to location of the holes at the distal end of the nail. The through holes in the proximal end of he nail are usually located by a fixture which positions itself relative to the top and accessible end of the intramedullary nail. The top of the intramedullary nail is usually accessible because it is at this location that the surgeon cuts through he leg of a person in order to gain access to the portion of the femur or tibia where the intramedullary nail will be inserted. Since this usually occurs at the proximal end of the bones, location of the proximal transverse holes is a task of medium difficulty.

Location of the transverse holes at the distal end of the bones is another matter completely. Because the intramedullary nail is not exposed at this end of the bone and because there is no incision at this portion of the person's body, x-ray apparatus in conjunction with various fixtures must be utilized to locate these transverse holes. Usually, in the prior art, a targeting device which utilizes the proximal end of the bone as a reference location is placed in the vicinity of the distal transverse hole or holes. Then, utilizing a combination and x-rays and an imaging intensifier, the targeting device is hopefully aligned perfectly with the hole in the distal end of the bone. This is a trial and error procedure and is very difficult. Many times, a number of attempts must be made before the hole is finally located and the fastening device inserted therethrough.

Accordingly, a primary object of the present invention is to provide an intramedullary nail which will allow proper fixation of a closed, an open, or any other type of break or fracture of the femur or tibia.

Another object of the present invention is to provide an intramedullary nail which will allow for reconstruction of femoral and tibial bone fractures wherein the reconstructed bone is properly aligned as to transverse, axial and rotational aspects and provides for the proper pre-fracture length of the bone.

Another object of the present invention is to provide an intramedullary nail for the proper fixation of a broken tibia or femur bone, where the fracture involves a simple closed transverse fracture, a segmented fracture, a rotationally unstable fracture, comminuted fracture, or a fracture with bone loss.

Another object of the present invention is to provide an intramedullary nail which allows for fixation of proximal fractures of a femur bone including fractures across the neck thereof.

Another object of the present invention is to provide an intramedullary nail which allows for proper fixation of fractures of the distal end of a femur or a tibia.

The above-stated objects as well as other objects which although not specifically stated, but are intended to be included within the scope of the present invention, are accomplished by the present invention and will become apparent from the hereinafter set forth Detailed Description of the Invention, Drawings, and the Claims appended herewith.

SUMMARY OF THE INVENTION

The present invention accomplishes the above-stated objectives as well as others, and comprises an improved two-piece intramedullary nail; a stem portion and a rod portion.

The stem portion of the inventive intramedullary nail comprises an elongated rod having screw threads at both ends thereof with the distal screw thread comprising a lag screw thread having a diameter larger than the main stem diameter. The proximal end of the stem includes a conventional screw thread having an outer diameter the same diameter as the main portion of the stem. One or more axial grooves or slots are provided in the distal lag screw threaded end of the stem for alignment with a key member of the rod portion of the nail. The groove and key provide for anti-rotational motion of the rod portion relative to the stem portion of the intramedullary nail.

The rod portion of the nail comprises an elongated hollow rod which fits over the stem portion of the nail. The internal diameter of the rod portion includes a step at the location of the proximal end of the stem portion which provides for the fit up of a nut or compressive screw and thereby secures the stem portion in compressive alignment with the rod portion of the nail. The distal end of the rod portion includes one or more extending bar members which fit within the slotted portion of the lag screw of the stem portion. The proximal end of the rod portion includes an enlarged cylindrical member with a step between it and the juncture of the main portion of the rod portion of the nail. This step, in conjunction with a similar step machined into the proximal end of the femur or the tibia, provides a proximal anchor point for the intramedullary nail. Thus, the fixed location of the proximal and distal ends of the inventive intramedullary nail allow for placing of the broken femur or tibia in compression to compress a fracture anywhere along the length thereof.

An elongated slot in the center of the distal end of the stem which may be filled with a appropriate plastic material provides for the relatively easy fixation of the distal end of the intramedullary nail by use of a transverse screw fastener threaded through the plastic material within the slot. Similarly, an elongated slot at the proximal end of the rod portion of the intramedullary nail provides for relatively easy location and fixation of the proximal end of the intramedullary nail with regard to the proximal end of the femur or tibia by use of a transverse screw fastener threaded therethrough.

An angled hole through the enlarged cylindrical proximal end of the rod portion of the intramedullary nail allows for the fitting and location therein of a cylindrical portion of a hip prosthesis which may be used to secure a broken head of a femur or the attachment thereto of a replacement femoral head.

The elongated slot provided within the proximal end of the rod portion and another slot in the central portion of the intramedullary nail provide for the easy attachment of an axial bone fixation plate to a femur broken in one or more segments at this location.

BRIEF DESCRIPTION OF THE DRAWINGS

Various other objects, advantages, and features of the invention will become apparent to those skilled in the art from the following discussion taken in conjunction with the following drawings, in which:

FIG. 1 is an isometric view of the rod portion and the stem portion of the inventive intramedullary nail;

FIG. 2 is an assembled cross-sectional view of the intramedullary nail of FIG. 1 rotated 90°;

FIG. 2A is an enlarged view of the attachment of the stem to the rod;

FIG. 6 is a cross-sectional view of a half-length intramedullary nail being utilized to fix a segmented fracture across the proximal end of the femur;

FIG. 7 is a cross-sectional view of the distal end of the intramedullary nail being utilized to fix a fragmented fracture across the distal end of the femur;

FIG. 8 is a cross-sectional view illustrating the intramedullary nail in connection with a hip prosthesis for fixation of a broken head of a femur;

FIG. 9 is a cross-sectional view illustrating the proximal end of the intramedullary nail being utilized to attach thereto a femoral head hip prosthesis.

DESCRIPTION OF THE PREFERRED EMBODIMENTS

Figure 3:
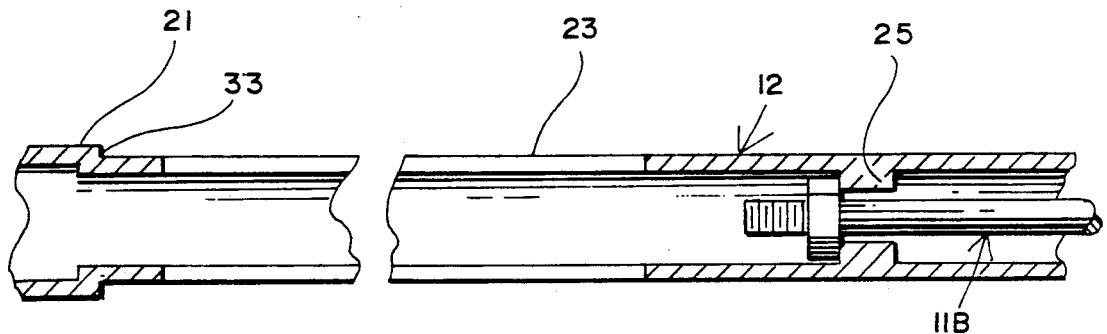
FIG. 3 is a cross-sectional assembled view of the intramedullary nail showing a stem attached to the approximate mid-portion of the rod portion of the nail.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various figures are designated by the same reference numerals.

Referring now to the various figures of the drawings, in FIG. 1 there is illustrated the inventive two-piece intramedullary nail 10 comprising a stem portion 11 and a rod portion 12. Stem portion 11 comprises an elongated rod having lag screw type threads 13 at the distal end thereof with a smaller diameter cylindrical portion 14 extending toward the proximal end thereof ending in screw threads 15 at the end thereof. An elongated slot 16 extending through the center thickness of lag screw portion 13 is provided. A filler material 17, which may comprises a high-density polyethylene or other appropriate material, fills center slot 16. Center slot 16 and filler material 17, as explained hereinafter, may be used to either provide a means for attaching locking screw fasteners at the distal end of the intramedullary nail 10 or to provide a means to fix broken segments of the distal end of a femur or tibia.

Rod portion 12 of intramedullary nail 10 comprises a hollow elongated rod member having an enlarged cylindrical portion 21 at the proximal end thereof and one or more extending bar members 22 integrally attached to the distal end thereof. Rod portion 12 may include a proximal slot 23 and a distal slot 24 through the walls of rod member 12. The distal end of rod portion 12 includes a flange member 25 integrally connected to the inside diameter of rod member 12 for purposes of securing stem member 11 to rod member 12. A hole 26 through flange member 25 permits fitting therethrough of the cylindrical and threaded rod portion 15 of stem member 11. One or more grooves 27 extending along the length of lag screw portion 13 of stem member 11 provides for rotational alignment of stem member 11 with regard to rod member 12 by means of extending bar members 22 which fits within slots 27. An opening 31 angled transversely with regard to the axial centerline of rod member 12 is provided in proximal end 21 of rod member 12 for purposes of fitting therewithin and securing thereto a hip undo prosthesis or a femoral head fixation plate.

FIGS. 2 and 2A illustrate the fitting of intramedullary nail 10 within a cavity within a femur. The intramedullary nail 10 shown in FIG. 2 is rotated 90 relative to that shown in FIG. 1 and is seen to be slightly bent to the curvature of a femur. Here the stem member 11 is shown being fitted within rod member 12 As can be seen, threaded portion 15 fits through hole 26 in flange member 25 and extends therethrough. A nut 28 threaded onto end 15 bears up against flange 25 and when further tightened causes compression of the femur between lag screw threaded portion 13 of stem member 11 and step 33 at the proximal end of rod member 12. Thus, the arrangement shown in FIG. 2 may be utilized for a fracture of the femur at any location between the proximal and distal end thereof. The space 34 between stem member 11 and rod member 12 indicates that the femur is being compressed in order to fix the fracture thereof. Should the fracture of a femur be such 1 that there is loss of bone, an appropriate plurality of circular disc members 35 may be placed over the rod portion 14 of stem member 11 and be fitted within space 34 between stem member 11 and rod member 12. In this manner the correct length of the femur may be attained during fixation of a bone.

Figure 4:
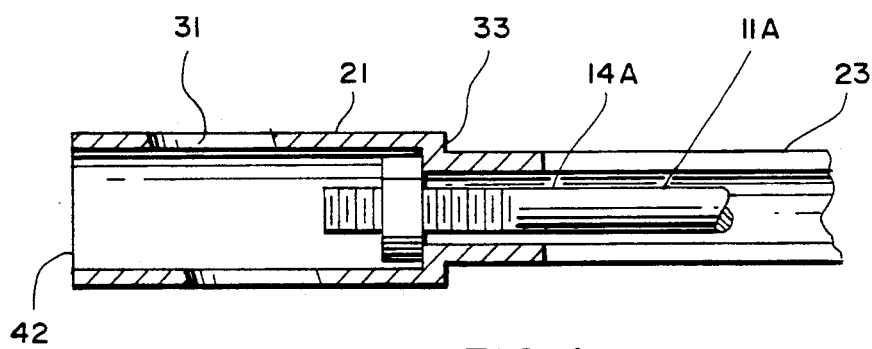
FIG. 4 is a cross-sectional view of the intramedullary nail showing the stem portion being connected at the proximal end of the rod portion.
Figure 5:
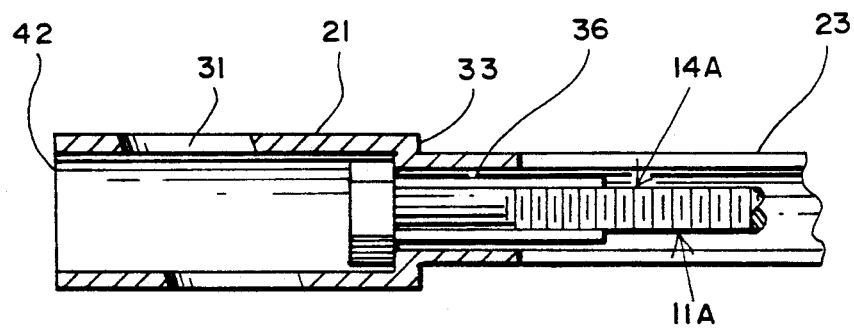
FIG. 5 is a cross-sectional view of the stem portion being connected at the proximal portion of the rod portion illustrating the use of a compressive screw.

In FIG. 3 a mid-length stem member 11B is utilized with rod member 12. In this embodiment flange portion 25 is located at the approximate mid-point of rod member 12. An intermediate length stem member 11B may be utilized so that the elongated proximal slot 23 is clear of stem member 11 and its attachment to rod member 12. In this regard it is to be noted that in the embodiment of FIG. 2 both the proximal elongated slot 23 is clear of stem member 11. In the embodiments of FIGS. 4 and 5, on the other hand, the proximal slot 23 is encumbered by the stem member 11A. If intramedullary nail 12 should be used for fixation of a fracture of a tibia, the curvature of intramedullary nail 10 would approximate that of a tibia.

In FIG. 4 the stem member 11A is seen to comprise an elongated rod portion 14A with a nut 27 bearing against the inner surface of step 33 and rod portion 12. The main difference between that of FIG. 2 and FIG. 4 is that the connection of the stem 11 to rod 12 is at different locations within the length of rod 12.

In FIG. 5 a different thread engagement technique is used compared to that of FIG. 4. In FIG. 5 a hollow bolt 36 secures the threaded end portion 15 of stem member 11A. Other obvious variations may also be utilized.

In the embodiment of FIG. 6, a shortened intramedullary nail 10A is utilized to fix a fracture segmented or otherwise of the proximal end of a femur. In this embodiment a shortened version of the stem member 11 is similar to that of FIG. 2 while a shortened version of rod member 12A is also utilized. One or more threaded screw fasteners 41 may be applied to the fragmented broken portion of the femur and extend through proximal slot 23 so as to secure the broken fragments thereof. The advent of elongated slot 23 does not necessitate time-consuming, trial-and-error procedures to locate screw fasteners 41 therewithin. The orientation of proximal slot 23 (and distal slot 24) may be with regard to a reference mark provided on the top end 42 of the proximal end 21 of rod member 12. Thus, the fit up of screw fasteners 41 within and through the rod member 12A does not necessitate the use of a targeting device in conjunction with an image intensifier and x-rays as required in the prior art.

In the event that the fractured femur also involves the fracture of the femoral head along the neck thereof, the inventive intramedullary nail 10 may be utilized in conjunction with a hip plate and screw prosthesis to secure the same. As seen in FIG. 8, hip plate and screw prosthesis 39 involves a plate 43, a cylindrical barrel 44 and lag screw 45. Hip prosthesis 39 may be secured to the femur by means of fasteners 46 which pass through the elongated proximal slot 23. Again, the position of slot 23 is a relatively easy matter to locate because of its size and does not require extensive fixtures or tooling. In this embodiment it is to be noted that the cylindrical barrel 44 of hip prosthesis 39 and its connection to plate 43 is provided with extra-firm structural support by means of the opening 31 within the proximal end of rod member 12 and within which barrel 44 is supported. In FIG. 9 it is seen how a fractured distal end of a femur or tibia may be fixed utilizing the intramedullary nail 10. In this embodiment a fastening device 47 is threaded through the various segments of the broken distal end of the femur while passing through the filled opening 16 in the lag screw portion 13 of stem member 11. Because of the relatively large size of the center slot 16, no special tooling or fixtures are required to fit fastening member 47 therethrough. The filler material 17 further secures fastener 47.

In FIG. 10 a femoral head hip prosthesis 51 is fitted b fasteners 52 which again pass through proximal elongated slot 31 of cylindrical portion 21 of rod 12. In this embodiment instead of a lag screw, an elongated rod 53 is secured within barrel 54 of hip prosthesis 51. Elongated rod 53 is adapted to receive an appropriate replacement head 55 which may be used to replace a damaged one. In this embodiment the fit up of cylinder 54 within slot 31 again provides for the structural support of the connection of cylinder 54 to plate 56 of prosthesis 51. In FIG. 6, an additional feature is presented. A fitting 61 is thread fastened within the opening 65 in cylindrical member 21. A hole 64 is provided axially throughout the length of fitting 61. A flexible tube 62 is attached to fitting 61. Flexible tube 62 provides an antibiotic source supply to fitting 61. The antibiotic flows through tubing 62, into and through fitting 61 and drops 63 interior through rod 12A to the site of the bone fracture 66. In this manner, an antibiotic may be directly directed to the fracture site.

While the invention has been described, disclosed, illustrated and shown in certain terms or certain embodiments or modifications which it has assumed in practice, the scope of the invention is not intended to be nor should it be deemed to be limited thereby and such other modifications or embodiments as may be suggested by the teachings herein are particularly reserved especially as they fall within the scope of the breadth and scope of the claims here appended.

I claim as may invention:

1. An intramedullary nail adapted for use with a fractured bone having an intramedullary canal therein comprising:
a stem member having a first threaded end and a second threaded end, said first threaded end being adapted to be threadingly connected to said intramedullary canal of said bone.
a rod member having an axial opening therethrough, having a first end and a first flange means there within fitting over the second send of said stem member which extends through said first flange means,
a fastening member attached to said second threaded end of said stem member and bearing against said flange means within said rod member said rod member having a second flange means at a second end thereof whereby said fractured bone is compressed between said first threaded end of said stem member and said second flange means on said rod member when said fastening member is tightened.

2. The apparatus of claim 1, including groove and key means between said rod and stem members for axially aligning said rod and stem members and preventing relative rotational motion between said rod and stem members.

3. The apparatus of claim 2, wherein said groove means comprises one or more grooves in the surface of said stem member in axial alignment with the longitudinal axis of said stem member.

4. The apparatus of claim 2, wherein said key means comprises one or more key members extending form said rod member in axial alignment with the longitudinal axis of said rod member.

5. The apparatus of claim 1, wherein said intramedullary nail further comprises an elongated opening through the thickness of said stem member.

6. The apparatus of claim 5, wherein said elongated opening through said stem member is filled with a plastic material.

7. The apparatus of claim 1, wherein said rod member further comprises one or more elongated slots provided transverse to the longitudinal axis through the thickness of said rod member and extending along the longitudinal length thereof.

8. The apparatus of claim 1, wherein said rod member further comprises a cylindrical member at one end thereof integrally connected to an elongated rod portion extending therefrom with said second flange means being between said cylindrical member and said elongated rod portion.

9. The apparatus of claim 1, wherein said rod member further comprises an angled hole through the thickness of said cylindrical member.

10. The apparatus of claim 1, wherein said intramedullary nail further comprises a hip plate and screw prosthesis having a cylindrical barrel member which passes through an inclined opening transversely through one end of said rod member and a plate member which is adapted to be fastened to the outer surface of a bone.

11. The apparatus of claim 1, wherein said intramedullary nail further comprises a femoral head hip prosthesis having a cylindrical member passing through an inclined opening transversely through one end of said rod member and a plate member which is adapted to be fastened to he under surface of a bone, said femoral head hip prosthesis having a femoral replacement head attached thereto.

12. The apparatus of claim 1, wherein said intramedcullary nail further comprises said rod member having an elongated slot through the thickness of said rod member, said elongated slot being fitted with a plastic material and one or more screw members adapted to pass transversely through said elongated slot of said rod member.

13. The apparatus of claim 1, wherein said intramedullary nail further comprises an elongated slot through the thickness of said stem member, said elongated slot being filled with a plastic material and a screw member adapted to pass transversely through said elongated slot of said stem member.

14. The intramedullary nail of claim 1, wherein said rod member is hollow and further comprises a hollow fitting attached to one end of said rod member, said fitting being adapted to be attached to a source of antibiotic whereby said antibiotic may be directed to said fracture of said bone.

15. The apparatus of claim 1 including an axial space between transverse surfaces of said rod and stem members said axial space being fitted with spacing means for maintaining a predetermined length of said intramedullary nail.

* * * * *